(12) United States Patent
Béjar et al.

(10) Patent No.: US 11,998,605 B2
(45) Date of Patent: Jun. 4, 2024

(54) STABILIZED AQUEOUS COMPOSITIONS OF NEUROMUSCULAR BLOCKING AGENTS

(71) Applicant: B. Braun Melsungen AG, Melsungen (DE)

(72) Inventors: Juan Gil Béjar, Rubi (ES); Cristina Timoneda Ramia, Barcelona (ES)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 16/515,653

(22) Filed: Jul. 18, 2019

(65) Prior Publication Data

US 2020/0000925 A1    Jan. 2, 2020

Related U.S. Application Data

(63) Continuation of application No. 14/420,684, filed as application No. PCT/EP2013/069507 on Sep. 19, 2013, now abandoned.

(30) Foreign Application Priority Data

Sep. 27, 2012  (EP) .................................. 12186393

(51) Int. Cl.
*A61K 47/26* (2006.01)
*A61K 9/00* (2006.01)
(Continued)

(52) U.S. Cl.
CPC ............ *A61K 47/26* (2013.01); *A61K 9/0019* (2013.01); *A61K 31/58* (2013.01); *A61K 45/06* (2013.01); *A61K 47/12* (2013.01)

(58) Field of Classification Search
CPC .......... A61K 31/58; A61K 47/26; A61K 9/08; A61K 47/12
See application file for complete search history.

(56) References Cited

U.S. PATENT DOCUMENTS

| 5,478,829 A | 12/1995 | Conrath |
| 7,838,515 B2 * | 11/2010 | Anderson .............. A61K 47/24 514/642 |

(Continued)

FOREIGN PATENT DOCUMENTS

| EP | 0 707 853 A1 | 4/1996 |
| EP | 2 462 913 A1 | 6/2012 |

(Continued)

OTHER PUBLICATIONS

Data Sheet for DBLTM Rocuronium Bromide Injection; https://www.medsafe.govt.nz/profs/Datasheet/d/dblrocuroniuminj.pdf, dated Sep. 30, 2010; accessed from https://web.archive.org/web/20121013134544/http://www.medsafe.govt.nz/profs/Datasheet/d/dblrocuroniuminj.pdf; accessed May 17, 2021 (Year: 2010).*

(Continued)

*Primary Examiner* — Timothy P Thomas
(74) *Attorney, Agent, or Firm* — Christopher A. Rothe; Culhane PLLC

(57) ABSTRACT

The present invention relates to an aqueous composition comprising:
(i) a steroidal neuromuscular blocking agent that is a Rocuronium salt, further wherein the steroidal neuromuscular blocking agent is present at a concentration ranging from 5 mg/mL to 20 mg/mL based on the total volume of the aqueous composition; and
(ii) an excipient that includes D-gluconic acid, D-glucono-delta-lactone, or a combination thereof, where the steroidal neuromuscular blocking agent and the excipient are dissolved in a solution consisting of water.
Furthermore the present invention relates to a liquid pharmaceutical composition comprising or consisting of said aqueous composition and a method for producing said aqueous composition.

11 Claims, 2 Drawing Sheets

(51) Int. Cl.
*A61K 31/58* (2006.01)
*A61K 45/06* (2006.01)
*A61K 47/12* (2006.01)

(56) References Cited

U.S. PATENT DOCUMENTS

| | | |
|---|---|---|
| 2006/0148841 A1 | 7/2006 | Lundeen |
| 2006/0229258 A1 | 10/2006 | Serikaku |
| 2006/0275331 A1 | 12/2006 | Zaludek et al. |
| 2010/0082749 A1 | 4/2010 | Zaludek et al. |
| 2010/0093849 A1* | 4/2010 | Zaludek ............... A61K 9/0019 514/492 |
| 2010/0286075 A1 | 11/2010 | Lee et al. |
| 2011/0178068 A1 | 7/2011 | Almarsson et al. |

FOREIGN PATENT DOCUMENTS

| | | |
|---|---|---|
| WO | WO 00/44334 A2 | 8/2000 |
| WO | WO 2005/025551 A2 | 3/2005 |
| WO | WO 2008/054142 A1 | 6/2008 |
| WO | WO 2008/089709 A2 | 7/2008 |

OTHER PUBLICATIONS

Data Sheet for DBLTM Rocuronium Bromide Injection (https://www.medsafe.govt.nz/profs/Datasheet/d/dblrocuroniuminj.pdf, dated Sep. 30, 2010 (Year: 2010).*

Mohan; "Calbiochem: Buffers: A guide for the preparation and use of buffers in biological systems"; 2003; http://wolfson.huji.ac.il/purification/PDF/Buffers/Calbiochem_Buffers_Booklet.pdf; accessed May 13, 2022 (Year: 2003).*
Abstract of Chinese Patent—CN1864667, Nov. 22, 2006, 1 page.
Abstract of German Patent—DE10337710, Mar. 10, 2005, 1 page.
Abstract of Article—R. E. Deákne et al., "Pharmaceutical development of injectable Arduan," *Acta Pharmaceutical Hungarica*, May 1992, vol. 62, No. 3, pp. 115-120.
Article—C. Lee, "Structure, conformation, and action of neuromuscular blocking drugs," *British Journal of Anaesthesia*, vol. 87, No. 5, 2001, pp. 755-769.
Article—Anonymous, *Stable Parenteral Composition of Quaternary Ammonium Neuromuscular Block Agent and Process of Preparation Thereof*, www.ip.com. Oct. 31, 2008, 8 pages.
Benet et al., "BDDCS Applied to OVER 900 Drugs"; 2011; The AAPS Journal; 13(4); DOI: 10.1208/S 12248-011-9290-9 (Year: 2011), pp. 519-547.
Translation—Fedotov, V.D., Large Dictionary of Medical Terms.—M.: Zao Tsentrpoligraph, 2007, p. 530.
Nakov, et al., "Determination of Rocuronium bromide by hydrophilic interaction liquid chromatography (HILIC)", Macedonian pharmaceutical bulletin, 57 (1,2), 2011, pp. 17-24.
"SIDS Initial Assessment Report for SIAM 18", Paris, France, Apr. 2004, pp. 20-23.
Stranz, et al., "A Review of pH and Osmolarity", International Journal of Pharmaceutical Compounding, vol. 6, No. 3, May/Jun. 2002, pp. 216-220.
International Search Report for PCT/EP2013/069507 dated Dec. 9, 2013, 3 pages.

* cited by examiner

STABILIZED AQUEOUS COMPOSITIONS OF NEUROMUSCULAR BLOCKING AGENTS

CROSS REFERENCE TO RELATED APPLICATIONS

This application is a continuation application of U.S. patent application Ser. No. 14/420,684 having a filing date of Feb. 10, 2015, which is the national stage entry of International Patent Application No. PCT/EP2013/069507 having a filing date of Sep. 19, 2013, which claims priority to and the benefit of European Patent Application No. 12186393.0 filed in the European Patent Office on Sep. 27, 2012, the entire contents of which are incorporated herein by reference.

FIELD OF THE INVENTION

The invention relates to an aqueous composition comprising a quaternary ammonium blocking agent and a polyhydroxy acid based excipient, and a method for producing said composition. Furthermore, the invention relates to a liquid pharmaceutical composition comprising said aqueous composition. The compositions of the present invention can further be comprised in a container made of glass or an organic polymer. Additionally, the invention relates to a pharmaceutical kit comprising the compositions of the present invention.

BACKGROUND OF THE INVENTION

Anesthesia is typically defined as the elimination of certain body functions of a patient so that diagnostic or surgical procedures can be tolerated. Traditionally, anesthesia comprises the components of pain relief (analgesia), loss of consciousness (hypnosis), loss of vegetative functions and muscle relaxation (paralysis). These effects can be obtained from a single drug which alone provides the correct combination of effects, or a combination of drugs (such as hypnotics, sedatives, paralytics and analgesics) to achieve very specific combinations of results.

Typically, in order to obtain the relaxation of skeletal muscles neuromuscular blocking agents are employed. Their rapid onset and short-acting behavior are key features to the success of these drugs. For example, in addition to the general relaxation of skeletal muscles to exclude uncontrolled movements of the patient during surgery neuromuscular blocking agents can be used to paralyze the vocal cords permitting intubation of the trachea or to inhibit spontaneous ventilation.

A review article on the structure, conformation and action of the state of the art neuromuscular blocking drugs is available from C. Lee, Br. J. Anaesth. 2001, 87 (5), 755-769.

Most neuromuscular blocking agents currently available have a quaternary ammonium structure. Such a structure allows for binding to the postsynaptical nicotinic acetylcholine receptor thereby inhibiting or interfering with the binding of acetylcholine to the receptor finally leading to muscle relaxation.

Typically, the neuromuscular blocking agents are applied by intravenous injection. This requires dissolving the mostly freeze-dried powders containing the active ingredient and excipients in a solvent containing water for injection and optional co-solvents. Recently, new dosage forms have been developed providing ready-to-use products which are already dissolved. These pre-diluted products comprising the pharmaceutical compounds are however highly unstable and require cool chain shipment and storage. This is highly inconvenient and costly.

The stability of neuromuscular blocking agents in solution has been addressed in the past. For example, EP-B-0707853 describes a pharmaceutical composition containing an effective amount of a neuromuscular blocking agent and from 0.01 to 30% of at least one zwitterionic substance as a stabilizer. Examples of such suitable zwitterionic substances include amino acids with an isoionic point not higher than 7, in particular, glycine, serine, methionine, alanine, isoleucine, leucine, phenylalanine, proline, hydroxyproline, tryptophan, tyrosine, valine and cysteine.

EP-A-1874319 describes muscle relaxant formulations which include one or more quaternary ammonium neuromuscular blocking agents having a reduced tendency for hydrolytic degradation, and therefore longer shelf life stability, when combined with one or more organic anions having at least six carbon atoms and having a pKa of less than 4.0. The organic anions can be selected from the group consisting of gentisic acid, saccharin, glycocholic, benzenesulfonic, toluenesulfonic acid, N-acetyltryptophan and dimyristoyl phosphatidylglycerol.

WO2008/065142 describes a pharmaceutical composition in the form of an aqueous solution for parenteral administration comprising Rocuronium and a sulfoalkylether-beta-cyclodextrin derivative or a pharmaceutically acceptable salt thereof which can be stored at ambient temperature and/or at higher pH while maintaining an adequate shelf-life.

CN 1864667 B discloses freezed dried pharmaceutical compositions comprising Rocuronium Bromide and mannitol. However, aqueous formulations formed therefrom still suffer from an insufficient long term stability at elevated temperatures.

However, there is a constant need for formulations comprising neuromuscular blocking agents which are stable at room temperature and provide acceptable shelf life (about 18 to 24 months) required for shipment and storage leading to increased environmental sustainability, facilitated handling and reduced marketing and purchasing costs.

DETAILED DESCRIPTION

Figure 1:
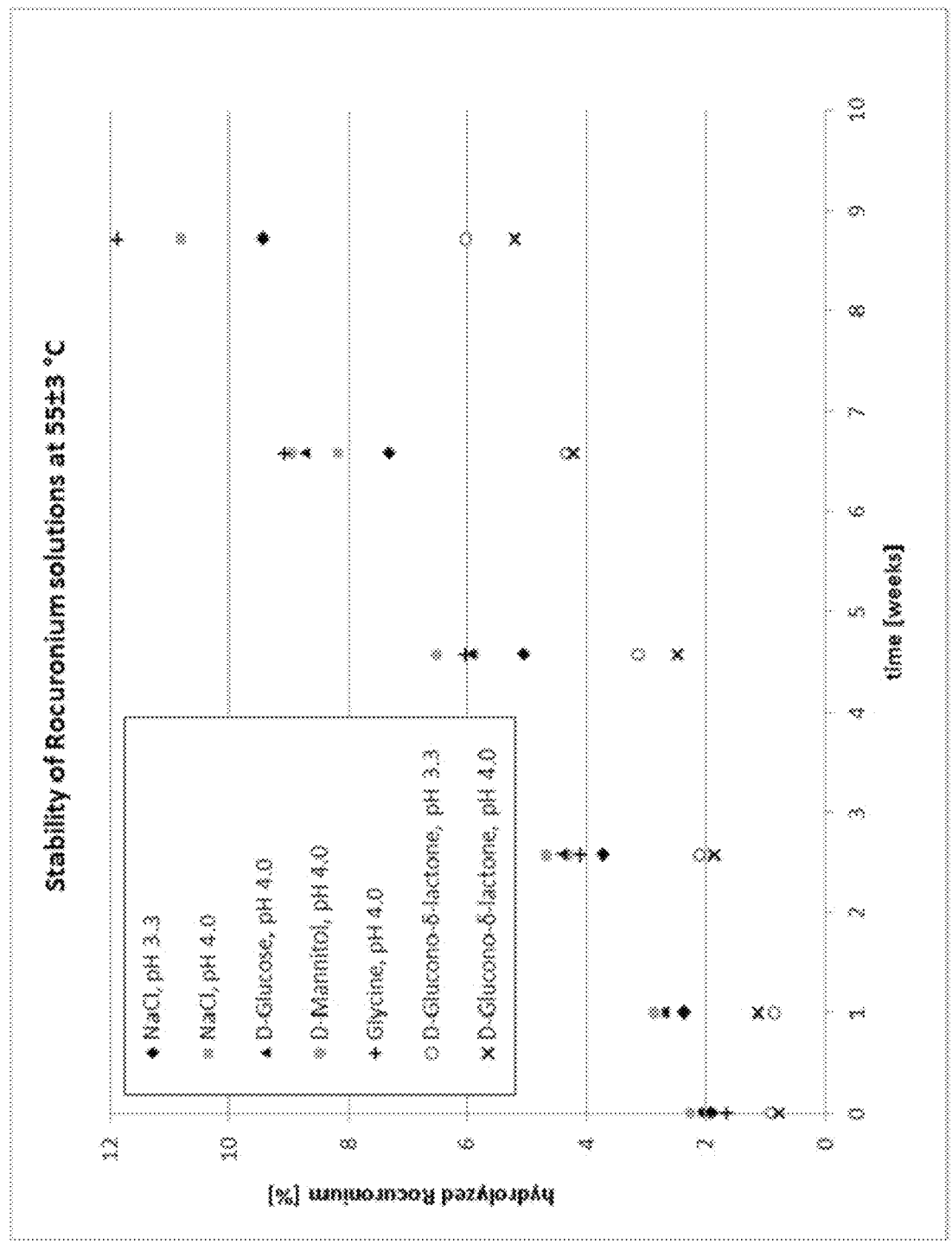
FIG. 1 is a diagram showing the concentration of hydrolyzed Rocuronium formed in solutions containing different excipients over time.

Unless otherwise noted, concentrations in mg/mL are based on the total volume of the aqueous composition and concentrations in % correspond to wt. % based on the total weight of the respective composition.

Throughout the formulas in the present description "Me" refers to methyl.

Quaternary Ammonium Neuromuscular Blocking Agent

The aqueous composition of the present invention comprises a quaternary ammonium neuromuscular blocking agent.

Preferably, the quaternary ammonium neuromuscular blocking agent is selected from the class of steroidal neuromuscular blocking agents.

Steroidal neuromuscular blocking agents are derived from a rigid bulky steroidal structure (see formula below) having substituents mimicking the structure of acetylcholine, i.e. the steroidal structure is typically substituted with one or more quaternary ammonium groups and one or more carboxylates.

Basic structure of steroidal compounds:

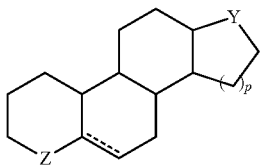

wherein p=1 or 2, Y and Z are independently selected from CH$_2$, O, NH or S, and $===$ is a single or double bond Acetylcholine:

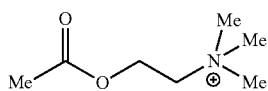

In one embodiment the quaternary ammonium neuromuscular blocking agent is derived from the following steroidal structure:

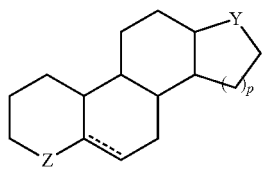

wherein p=1 or 2, Y and Z are independently selected from CH$_2$, O, NH or S, preferably Y and Z are both CH$_2$, $===$ is a single or double bond, and wherein the steroidal structure is further substituted with at least one carboxylate, at least one quaternary ammonium group and, optionally, one or more groups selected from alkyls and tertiary amines, or combinations thereof.

In a preferred embodiment the quaternary ammonium neuromuscular blocking agent is a compound of the following formula:

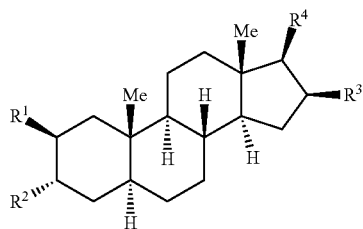

wherein R$^1$ and R$^3$ are independently selected from tertiary amines and quaternary ammonium groups, preferably, R$^1$ and R$^3$ are independently selected from cyclic tertiary amines and cyclic quaternary ammonium groups wherein the cycle optionally further contains one or more heteroatoms selected from nitrogen, oxygen or sulfur (i.e. one or more CH$_2$ groups in the cycle are substituted by optionally substituted heteroatoms), more preferably R$^1$ and R$^3$ are substituents of the following formulas:

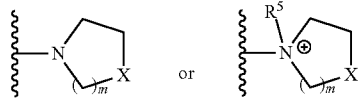

wherein m is an integer from 1 to 5, X=CH$_2$, NR$^7$, N$^+$R$^7$R$^8$, O or S (wherein R$^7$ and R$^8$ are independently H or C$_1$-C$_4$ alkyl, preferably H or Me) and R$^5$=C$_1$-C$_{10}$-alkyl or C$_2$-C$_{10}$-alkenyl; preferably m=1 or 2, X=CH$_2$, NR$^7$, N$^+$R$^7$R$^8$ or O (wherein R$^7$ and R$^8$ are independently H or C$_1$-C$_4$ alkyl, preferably H or Me) and R$^5$=methyl, ethyl, n-propyl, isopropyl, n-butyl, sec-butyl, isobutyl, tert-butyl, vinyl, allyl or butenyl.

In a preferred embodiment R$^1$ is selected from

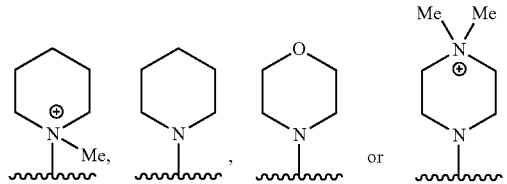

and R$^3$ is selected from

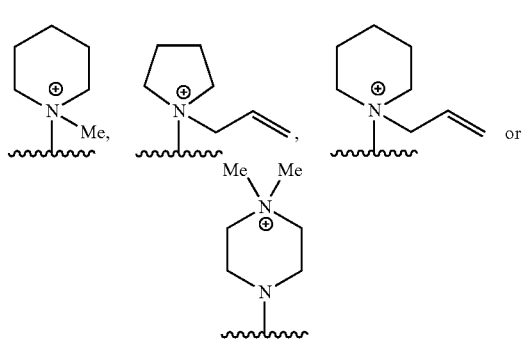

R$^2$ and R$^4$ are independently selected from hydroxyl or

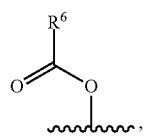

wherein R$^6$ is a C$_1$-C$_{10}$ alkyl, preferably C$_1$-C$_4$ alkyl, more preferably methyl or ethyl, with the proviso that at least one of R$^2$ or R$^4$ is

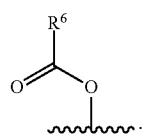

Exemplary quaternary ammonium neuromuscular blocking agents of the present are Pancuronium, Vecuronium, Rocuronium, Rapacuronium and Pipecuronium (Chart 1).

Chart 1. Selected quaternary ammonium neuromuscular blocking agents

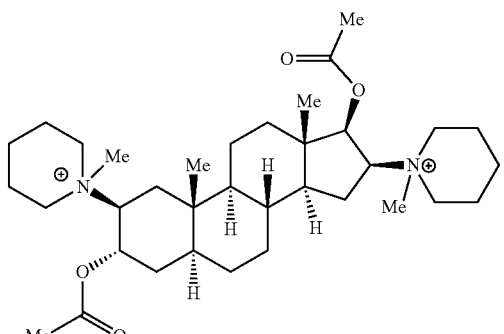

Pancuronium (Pavulon)

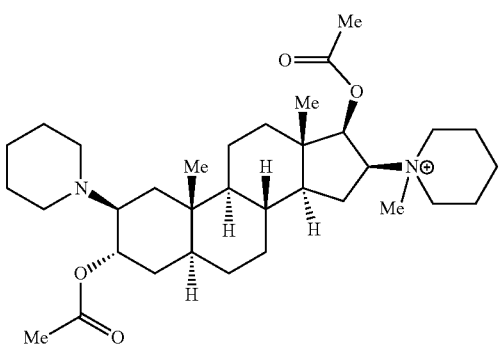

Vecuronium (Norcuron)

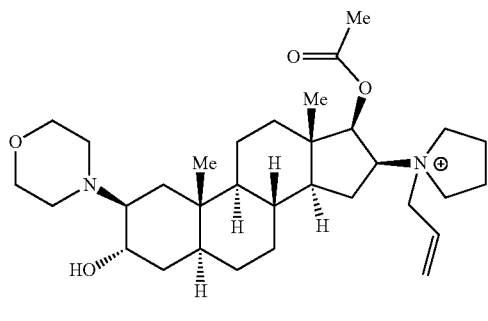

Rocuronium (Zemuron, Esmeron)

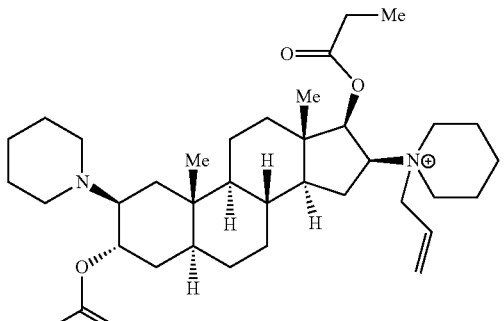

Rapacuronium (Raplon)

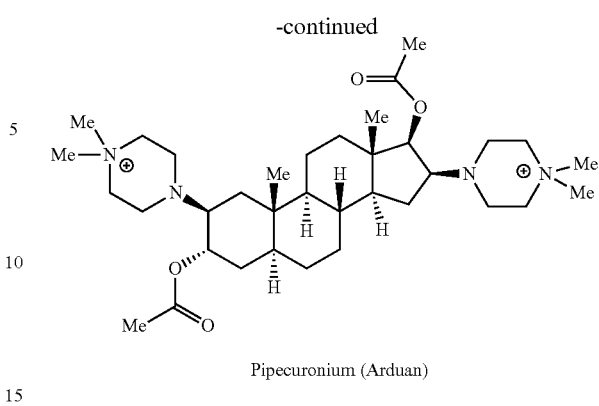

Pipecuronium (Arduan)

In the most preferable embodiment the quaternary ammonium neuromuscular blocking agent is a Rocuronium salt.

As apparent from the structure neuromuscular blocking agents described above may exist as ammonium salts. Pharmaceutically acceptable counter-anions include halides such as chlorides, bromides and iodides, sulfates, nitrates, tosylates, gluconates, acetates, formates, tartrates, etc. Most preferable are halides.

In a preferred embodiment of the invention the quaternary ammonium neuromuscular blocking agent is Rocuronium bromide.

Depending on the pH-value of the aqueous composition quaternary ammonium neuromuscular blocking agents can be protonated or de-protonated. For example, at a pH of up to about 6 Rocuronium is mainly present in the protonated form and at a pH of above 12 Rocuronium can be de-protonated:

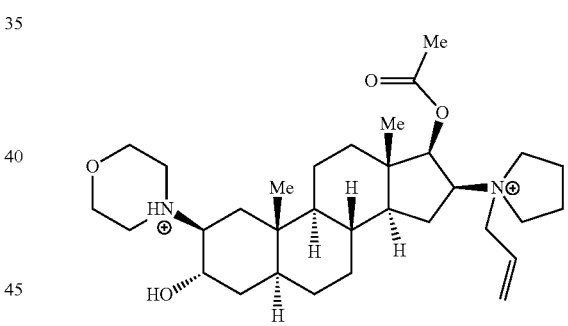

protonated form of Rocuronium

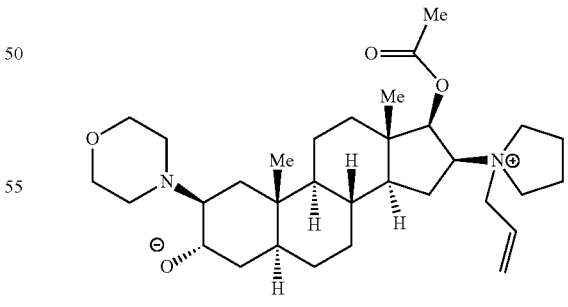

de-protonated form of Rocuronium

Accordingly, throughout the present description when referring to quaternary ammonium neuromuscular blocking agents any protonated or de-protonated form is included.

The concentration of the quaternary ammonium neuromuscular blocking agent is preferably in the range of about 1 to about 100 mg/mL based on the total volume of the aqueous composition, more preferably in the range of about 5 to about 50 mg/mL, most preferably from about 5 to about 15 mg/mL.

The shelf life of aqueous solutions of quaternary ammonium neuromuscular blocking agents at room temperature (25° C.) is significantly decreased by the formation of hydrolysis products. In particular, the carboxylate moieties are easily hydrolyzed to the corresponding carboxylic acids and alcohols (see exemplary hydrolysis of Rocuronium below). Under acidic conditions the hydrolysis is reversible. However, with an excess of water (such as in an aqueous solution) the equilibriums is almost completely on side of the hydrolysis products.

Under basic conditions the hydrolysis is almost irreversible (saponification). In order to inhibit the hydrolysis of the quaternary ammonium neuromuscular blocking agents, the solutions are typically cooled. However, such cooling is disadvantageous from an environmental and economical point of view.

Exemplary Hydrolysis of Rocuronium:

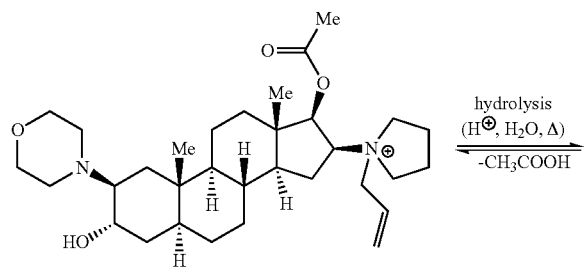 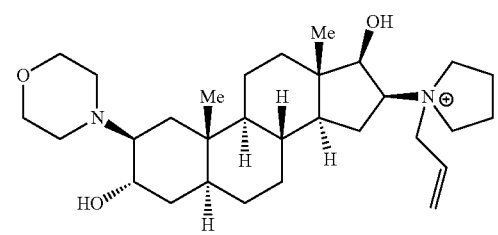

Polyhydroxy Acid and the Corresponding Lactones

It has surprisingly been found that the addition of an excipient selected from a polyhydroxy acid, the corresponding lactone thereof or a combination of both significantly stabilize aqueous solutions of quaternary ammonium neuromuscular blocking agents in that the hydrolytic degradation is inhibited.

The stabilization of the solutions does not only render the cooling of the formulations redundant but also allows for a thermal sterilization process (such as in an autoclave). Due to the thermal stability of the solution due to the presence of the excipients such thermal sterilization process does not negatively affect the product stability profile.

Accordingly, the aqueous composition of the present invention comprises an excipient selected from a polyhydroxy acid of the following formula: HO—CH$_2$—[CH(OH)]$_n$—COOH wherein n is an integer from 1 to 8, an intramolecular lactone thereof or a mixture of both.

Preferably, n is an integer from 2 to 6, more preferably, n is an integer from 3 to 5, most preferably n is 4.

The polyhydroxy acid of the present invention is preferably an aldonic acid, i.e., a polyhydroxy acid obtained from the oxidation of an aldose (wherein the aldehyde function of the aldose is oxidized to the carboxylic acid). The aldonic acid can be present in the respective D- or L-form. From an economical point of view the naturally occurring D-form is preferred.

Preferably the polyhydroxy acid of the present invention is the corresponding aldonic acid of an aldotetrose (n=2) such as erythrose, threose; an aldopentose (n=3) such as arabinose, lyxose, ribose, xylose; an aldohexose (n=4) such as allose, altrose, glucose, mannose, gulose, idose, galactose, talose; or an aldoheptose (n=5). More preferably, the polyhydroxy acid of the present invention is the corresponding aldonic acid of an aldohexose, most preferably the polyhydroxy acid is D-gluconic acid.

Depending on the pH value of the aqueous composition, the polyhydroxy acid can be present in the respective anionic form (carboxylate and/or alkoxide). Accordingly, throughout the present description when referring to polyhydroxy acids any protonated or de-protonated form is included. Preferred counter-cations are sodium, calcium, and potassium. For example, in water at a pH value of about 4 D-gluconic acid is present as mixture of D-gluconic acid to D-gluconate in a ratio of about 2:3.

The ratio of the polyhydroxy acid and corresponding carboxylate is preferably in the range of about 100:1 to about 1:100, more preferably in the range of about 50:1 to about 1:50, even more preferable in the range of about 20:1 to about 1:20, most preferably in the range of about 5:1 to about 1:5.

Alternatively, the aqueous composition of the present invention comprises a lactone of the above described polyhydroxy acids. A lactone is a cyclic ester which can be seen as the condensation product of an alcohol group —OH and a carboxylic acid group —COOH in the same molecule. The most stable structure for lactones are the 5-membered gamma-lactones and 6-membered delta-lactones because, as in all organic cycles, 5 and 6 membered rings minimize the strain of bond angles.

Preferably, the aqueous composition of the present invention comprises a delta-lactone of the aldonic acid of an aldohexose (n=4), preferably D-glucono-delta-lactone.

In aqueous solution, lactones can be hydrolyzed to the corresponding hydroxyl acids forming a mixture in constant equilibrium. This process can be affected by the concentration as well as the temperature of the solution. Accordingly, in a further embodiment of the invention, the aqueous composition comprises both the polyhydroxy acid and an intramolecular lactone thereof. Preferably, the aqueous composition of the present invention comprises a mixture of D-gluconic acid and D-glucono-delta-lactone.

The ratio of the polyhydroxy acid to the corresponding lactone is preferably in a range of about 100:1 to about 1:100, more preferably in the range of about 50:1 to about 1:50, even more preferable in the range of about 20:1 to about 1:20, most preferably in the range of about 5:1 to about 1:5.

The concentration of the excipient is preferably in the range of about 1 to about 100 mg/mL based on the total volume of the aqueous composition, more preferably in the range of about 5 to about 50 mg/mL, most preferably from about 15 to about 30 mg/mL.

Particularly Preferred Embodiments

In one embodiment, the present invention relates to an aqueous composition comprising:
(i) a quaternary ammonium neuromuscular blocking agent of the following formula:

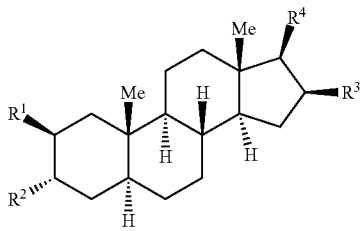

wherein $R^1$ and $R^3$ are independently selected from either

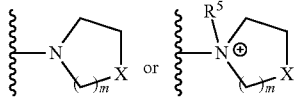

wherein m=1 or 2, $X$=$CH_2$, $NR^7$, $N^+R^7R^8$ or O (wherein $R^7$ and $R^8$ are independently H or $C_1$-$C_4$ alkyl) and $R^5$=methyl, ethyl, n-propyl, isopropyl, n-butyl, sec-butyl, isobutyl, tert-butyl, vinyl, allyl or butenyl, $R^2$ and $R^4$ are independently selected from hydroxyl or

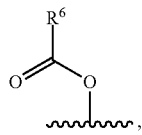

wherein $R^6$ is a $C_1$-$C_{10}$ alkyl, with the proviso that at least one of $R^2$ or $R^4$ is

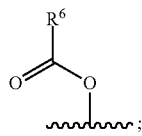

and
(ii) an excipient selected from a polyhydroxy acid of the following formula: HO—$CH_2$—[CH(OH)]$_n$—COOH, wherein n is an integer from 3 to 5, an intramolecular lactone of said polyhydroxy acid or a mixture thereof.

In a further embodiment the present invention relates to an aqueous composition comprising:
(i) a Rocuronium salt; and
(ii) an excipient selected from a polyhydroxy acid of the following formula: HO—$CH_2$—[CH(OH)]$_n$—COOH, wherein n is an integer from 3 to 5, an intramolecular lactone of said polyhydroxy acid or a mixture thereof.

In another embodiment, the present invention relates to an aqueous composition comprising:
(i) a quaternary ammonium neuromuscular blocking agent of the following formula:

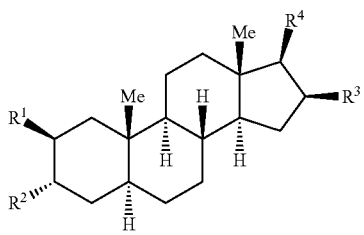

wherein $R^1$ and $R^3$ are independently selected from either

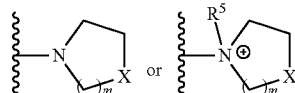

wherein m=1 or 2, $X$=$CH_2$, $NR^7$, $N^+R^7R^8$ or O (wherein $R^7$ and $R^8$ are independently H or $C_1$-$C_4$ alkyl) and $R^5$=methyl, ethyl, n-propyl, isopropyl, n-butyl, sec-butyl, isobutyl, tert-butyl, vinyl, allyl or butenyl, $R^2$ and $R^4$ are independently selected from hydroxyl or

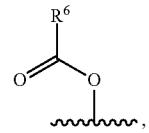

wherein $R^6$ is a $C_1$-$C_{10}$ alkyl, with the proviso that at least one of $R^2$ or $R^4$ is

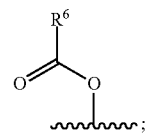

and
(ii) an excipient selected from D-gluconic acid, an intramolecular lactone of D-gluconic acid, preferably D-glucono-delta-lactone, or a mixture thereof.

In another embodiment, the present invention relates to an aqueous composition comprising:
(i) a Rocuronium salt; and
(ii) an excipient selected from D-gluconic acid, an intramolecular lactone of D-gluconic acid, preferably D-glucono-delta-lactone, or a mixture thereof.

Solvent

The main solvent of the aqueous composition of the present invention is water. Further co-solvents can be present in addition to water.

Suitable co-solvents for parenteral administration are benzyl benzoate, ethanol, glycerol, glycols such as propylene glycol and polyethylene glycol (especially PEG 300 and PEG 3350).

In a preferred embodiment the amount of water in the solvent is at least 50 wt. %, more preferably at least 80 wt. %, especially at least 95 wt. %, based on the total amount of solvent. Most preferably, water is the only solvent present in the aqueous composition of the present invention.

Buffer Agent

Furthermore, the aqueous composition of the present invention comprises an optional buffering agent. A buffering agent typically comprises a weak acid and its conjugate base or a weak base and its conjugate acid. Preferably, the buffering agent of the present invention is a buffer based on citrate, acetate, phosphate or a combination thereof. More preferably, the buffering agent of the present invention is a buffer based on citrate and acetate.

It has been found that the aqueous composition of the present invention can be even further stabilized when the pH value is adjusted from neutral to acidic, preferably acidic such as below a pH value below 7 or below 6. Preferably, the pH value of the aqueous composition of the present invention is in the range of about 2.0 or more to about 7.0 or less, more preferably from about 3.0 or more to about 5.0 or less, most preferably from about 3.8 or more to about 4.0 or less.

As known to the skilled person the pH value of the composition can be adjusted by the addition of suitable acids and bases such as, for example, acetic acid and sodium hydroxide.

Further Excipients

Further pharmaceutically suitable excipients which are usual in the art can be comprised in the compositions of the present invention including oil, preservatives, solubilizing, suspending, emulsifying or thickening agents, chelating agents, antioxidants and reducing agents, antimicrobial preservatives, bulking agents, protectants, tonicity adjustors, and special excipients etc. Preferably, said excipients are suitable for parenteral administration.

Suitable oils are for example peanut (groundnut) oil, cottonseed oil, soybean oil and sesame oil.

Suitable solubilizing, suspending, emulsifying or thickening agents are for example gum arabic (acacia gum), aluminum stearate, carboxymethyl cellulose (CMC), polyvinylpyrrolidone (PVP), sodium deoxycholate, lecithin, hydrolyzed collagen, polyoxyethylated fatty acids, polyoxyethylated castor oil, polysorbate 80 and 20, sodium dodecyl sulfate (SDS) and sorbitol.

Suitable chelating agents are for example various EDTA salts.

Suitable antioxidants and reducing agents are for example ascorbate, sodium sulfite, sodium bisulfite, sodium metabisulfite, thioglycerol, butylated hydroxyanisol (BHA), butylated hydroxytoluene (BHT) and cysteine.

Suitable preservatives are for example benzalkonium chloride, benzethonium chloride, benzyl alcohol, chorobutanol, parabens, phenol, 2-phenoxyethanol and thiomersal (thimerosal).

Suitable bulking agents, protectants or tonicity adjustors are for example salts such as sodium chloride, potassium chloride, sodium sulfate, magnesium chloride, magnesium sulfate and calcium chloride, amino acids such as alanine, arginine, asparagine, aspartic acid, glycine and histidine and albumin, hydrolysed collagen, glucose, sucrose, mannitol, inositol, sorbitol, lactose, citric acid, imidazol, PEG 3350, PVP and polysorbate 80.

Special excipients are for example gamma-cyclodextrins, aluminum hydroxide, aluminum phosphate, poly(lactic acid) (PLA), poly(lactic-co-glycolic acid) (PLGA), silica, zinc, protamine and sodium saccharine.

Preferably the amount of further excipients is generally less than 10 wt. % based on the total composition, more preferable less than 5 wt. %, especially less than 1 wt. %.

Preparation

The composition of the present invention can easily be prepared.

The method for preparing the aqueous composition of the present invention comprises:
- Providing a quaternary ammonium neuromuscular blocking agent, wherein the quaternary ammonium neuromuscular blocking agent can optionally be freeze dried.
- Providing an excipient selected from a polyhydroxy acid of the following formula: $HO—CH_2—[CH(OH)]_n—COOH$, wherein n is an integer from 1 to 8, an intramolecular lactone of said polyhydroxy acid or a mixture thereof, wherein said excipient is optionally freeze-dried.
- Mixing the quaternary ammonium neuromuscular blocking agent and the excipient in water (preferably water for injection) to give a liquid aqueous composition (preferably a solution).

Preferred embodiments with respect to the quaternary ammonium neuromuscular blocking agent and the excipient are described above in more detail.

Freeze-drying is particularly useful for the preservation of very sensitive (in particular temperature sensitive) quaternary ammonium neuromuscular blocking agents and excipients.

The quaternary ammonium neuromuscular blocking agent is preferably added at a concentration from about 1 to about 100 mg/mL based on the total volume of the aqueous composition, more preferably from about 5 to about 50 mg/mL, most preferably from about 5 to about 15 mg/mL. The Excipient is preferably added at a concentration from about 1 to about 100 mg/mL, more preferably from about 5 to about 50 mg/mL, most preferably from about 15 to about 30 mg/mL.

The weight ratio of quaternary ammonium neuromuscular blocking agent to excipient is preferably in the range of about 0.5:1 to about 1:5, more preferably in the range of about 1:1 to about 1:4, most preferably in the range of about 1:2 to about 1:3.

Optionally a buffer agent such as a mixture of sodium citrate and sodium acetate, can be added. The concentration of the buffer is preferably in the range from about 0.5 to about 50 mg/mL based on the total volume of the aqueous composition, more preferable from about 1 to about 25 mg/mL, most preferably from about 5 to about 10 mg/mL. The composition is preferably adjusted to a pH value of in the range of about 2.0 or more to about 7.0 or less, more preferably from about 3.0 or more to about 5.0 or less, most preferably from about 3.8 or more to about 4.0 or less. The pH value of the composition can be adjusted by the addition of suitable acids and bases such as acetic acid and sodium hydroxide.

Furthermore, the osmolality of the composition can optionally be adjusted. For example, the adjustment can be carried out by adjusting the concentration of the excipient and/or by the addition of further tonicity agents such as NaCl. The osmolality of the aqueous composition is preferably in the range of about 270 to about 340 mOsm/kg, more preferably in the range of about 285 to about 315 mOsm/kg The temperature during the preparation of the composition is preferably in the range of from about 5 to about 50° C., more preferably in the range of about 15 to about 50° C. and more preferably in the range of about 18 to about 30° C.

Particularly Preferred Embodiments

In a particularly preferred embodiment the method for preparing the aqueous composition of the present invention comprises:

Providing a quaternary ammonium neuromuscular blocking agent of the following formula:

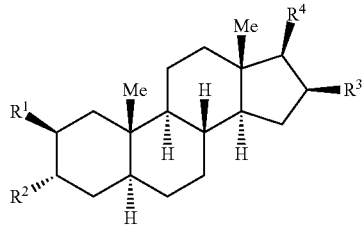

wherein $R^1$ and $R^3$ are independently selected from either

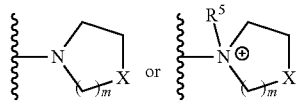

wherein m=1 or 2, $X=CH_2$, $NR^7$, $N^+R^7R^8$ or O (wherein $R^7$ and $R^8$ are independently H or $C_1$-$C_4$ alkyl) and $R^5$=methyl, ethyl, n-propyl, isopropyl, n-butyl, sec-butyl, isobutyl, tert-butyl, vinyl, allyl or butenyl, $R^2$ and $R^4$ are independently selected from hydroxyl or

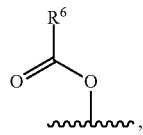

wherein $R^6$ is a $C_1$-$C_{10}$ alkyl, with the proviso that at least one of $R^2$ or $R^4$ is

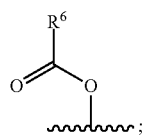

Providing an excipient selected from a polyhydroxy acid of the following formula: HO—$CH_2$—[CH(OH)]$_n$—COOH, wherein n is an integer from 3 to 5, an intramolecular lactone of said polyhydroxy acid or a mixture thereof;

Mixing the quaternary ammonium neuromuscular blocking agent and the excipient in water for injection to give a liquid aqueous composition (preferably a solution), wherein the concentration of the quaternary ammonium neuromuscular blocking agent is in the range of about 1 to about 100 mg/mL and the concentration of the excipient is in the range of about 1 to about 100 mg/mL based on the total composition of the aqueous composition.

In a further embodiment the method for preparing the aqueous composition of the present invention comprises:

Providing a quaternary ammonium neuromuscular blocking agent of the following formula:

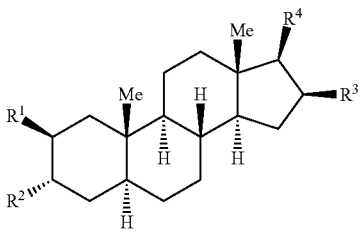

wherein $R^1$ and $R^3$ are independently selected from either

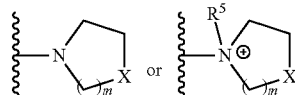

wherein m=1 or 2, $X=CH_2$, $NR^7$, $N^+R^7R^8$ or O (wherein $R^7$ and $R^8$ are independently H or $C_1$-$C_4$ alkyl) and $R^5$=methyl, ethyl, n-propyl, isopropyl, n-butyl, sec-butyl, isobutyl, tert-butyl, vinyl, allyl or butenyl, $R^2$ and $R^4$ are independently selected from hydroxyl or

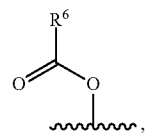

wherein $R^6$ is a $C_1$-$C_{10}$ alkyl, with the proviso that at least one of $R^2$ or $R^4$ is

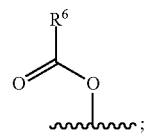

Providing an excipient selected from D-gluconic acid, an intramolecular lactone of D-gluconic acid, preferably D-glucono-delta-lactone, or a mixture thereof;

Mixing the quaternary ammonium neuromuscular blocking agent and the excipient in water for injection to give a liquid aqueous composition (preferably a solution), wherein the concentration of the quaternary ammonium neuromuscular blocking agent is in the range of about 1 to about 100 mg/mL and the concentration of the excipient is in the range of about 5 to about 50 mg/mL based on the total volume of the aqueous composition.

In another embodiment the method for preparing the aqueous composition of the present invention comprises:

Providing a Rocuronium salt;

Providing an excipient selected from a polyhydroxy acid of the following formula: HO—$CH_2$—[CH(OH)]$_n$—COOH, wherein n is an integer from 3 to 5, an intramolecular lactone of said polyhydroxy acid or a mixture thereof;

Mixing the Rocuronium salt and the excipient in water for injection to give a liquid aqueous composition (preferably a solution), wherein the concentration of the Rocuronium salt is in the range of about 5 to about 50 mg/mL and the concentration of the excipient is in the range of about 1 to about 100 mg/mL based on the total volume of the aqueous composition.

In a preferred embodiment the method for preparing the aqueous composition of the present invention comprises:

Providing a Rocuronium salt;

Providing an excipient selected from D-gluconic acid, an intramolecular lactone of D-gluconic acid, preferably D-glucono-delta-lactone, or a mixture thereof, Mixing the Rocuronium salt and the excipient in water for injection to give a liquid aqueous composition (preferably a solution), wherein the concentration of the Rocuronium salt is in the range of about 5 to about 50 mg/mL and the concentration of the excipient is in the range of about 5 to about 50 mg/mL based on the total volume of the aqueous composition.

Pharmaceutical Composition

The aqueous composition of the present invention is suitable to be used as a pharmaceutical composition. Accordingly, a further embodiment of the present invention relates to a liquid pharmaceutical composition comprising or consisting of the aqueous composition of the present invention. For pharmaceutical applications, the aqueous composition of the present invention is preferably a solution and injectible, and especially the pharmaceutical composition can be parenterally administered. Furthermore, the osmolality of the aqueous composition is preferably in the range of about 270 to about 340 mOsm/kg, more preferably the osmolality of the aqueous composition is in the range of about 285 to about 315 mOsm/kg.

The pharmaceutical compositions can be used in anesthesia, in particular for the relaxation of skeletal muscles which is for example required during surgery or mechanical ventilation or for the facilitation of endotracheal intubation. However, as patients are still aware of pain after full relaxation of the muscles, a general anesthetic and/or analgesic should be given to the patient to prevent anesthesia awareness.

In a particularly preferred embodiment the present invention relates to a liquid pharmaceutical composition for parenteral administration comprising:

5-20 mg/mL Rocuronium bromide, 15-35 mg/mL of a mixture comprising D-gluconic acid and the respective lactones thereof, and 1-10 mg/mL buffering agent comprising acetate and citrate based on the total volume of the liquid pharmaceutical composition, in water, wherein the pH of the composition is in the range of 3.8 to 4.0 and the osmolality is in the range of 285 to 315 mOsm/kg.

The pharmaceutical composition can be administered for example by injection or infusion.

Furthermore, the aqueous composition of the present invention can be part of a medical kit which is ready for clinical use. Such kits typically comprise two or more compartments containing supplies and, optionally, equipment for direct clinical use. The kits of the present invention can, for example, comprise additional relevant medication such as additional paralytics, general anesthetics, local anesthetics, sedatives, hypnotics, and/or analgesics.

Container

The aqueous composition of the present invention can be contained in a container made of glass or organic polymers such as polyethylene and/or polypropylene which may be permeable for oxygen. Containers, such as vials or ampoules made of organic polymers are advantageous since they do not break and the handling is easier. Preferably, the organic polymer is semipermeable for oxygen.

Preferably the container is free of PVC (polyvinyl chloride), DEHP (Bis-(2-ethylhexyl) phthalate) and latex (natural rubber). Suitable containers are for example available under the trade name Mini-Plasco® (BBraun Melsungen, Germany).

EXAMPLES

Materials:

The following materials have been received from commercial suppliers and have been used as received without any additional treatment:

Rocuronium bromide: Farmahispania S.A., Spain, injectable grade,

Sodium acetate.$3H_2O$: Verdugt B.V., Germany,

NaOH: 1 mol/l (1N) SV, PANREAC QUIMICA S.L.U., Spain,

Acetic acid (glacial): (Reag. Ph. Eur.) PA-ACS-ISO, PANREAC QUIMICA S.L.U., Spain, Sodium chloride: Esco France S.A.S., France, D-Glucose monohydrate: Cargill S.L.U., Spain, D-Mannitol: Roquette, S.A., France, D-(+)-Glucono-delta-lactone: Sigma-Aldrich Quimica SA, Spain, Sodium glycerophosphate.$5H_2O$: Dr. Paul Lohmann GmbH KG, Germany, L-Serine: 99% PS, PANREAC QUIMICA S.L.U., Spain, Glycine: (RFE, USP, BP, Ph. Eur.) PRS-CODEX, PANREAC QUIMICA S.L.U., Spain, Hydroxyethyl starch (HES): BBraun Crissier (Switzerland), molar substitution degree of 0.55, average molecular weight (Mn) of 70,000, C2/C6 ratio of 2 to 7.

Solutol® HS 15 and Kollidon® 12PF have been obtained from BASF (Germany).

The solubilizer Solutol® HS 15 (polyethylene glycol 660—12-hydroxystearate) is a non-ionic surfactant produced from 12-hydroxystearic acid and ethylene oxide. Kollidon® 12PF comprises soluble polyvinylpyrrolidone.

Water for injection (WFI) has been received from BBraun Rubi (Spain).

Example 1

Hydrolysis of Rocuronium (48 days, 40° C./55° C.)

In 20 mL colorless glass vials Rocuronium bromide (10 mg/mL), the excipients (see Table 1) and sodium acetate.$3H_2O$ (2.0 mg/mL) have been dissolved in water. In case of HES, Solutol® and Kollidon® 0.33% NaCl has been added to the solution as tonicity agent. The pH value of the solution has been adjusted to 4.0 by the addition of acetic acid (50% v/v) or sodium hydroxide (1.0 M). Then the formulations were autoclaved using overkill sterilization cycle (121° C., 15 min). The samples were then stored at 40±2° C. and 55±3° C. in a stability chamber and the formulations were analyzed after 6, 17, 33 and 48 days. The assessment of the stability of the solutions has been made on basis of the appearance of the solutions, the pH-value, osmolality, content of Rocuronium and its respective hydrolyzed product (Des-17-Acetyl-Rocuronium) determined by HPLC (method adapted for Rocuronium Bromide, British Pharmacopoeia 2008).

The relative stability results of the 48-day-study are shown in Table 1.

TABLE 1

48-days-stability-study

| Sample | Excipient | (mg/mL) | pH adjustment to pH = 4 | Theoretical osmolality (mOsm/Kg) | Stability after 48 d |
|---|---|---|---|---|---|
| 1 | NaCl | 3.3 | Acetic acid | 242 | 0 |
| 2 | D-glucose | 20.0 | 50% v/v | 240 | 0 |
| 3 | D-mannitol | 20.0 | | 239 | 0 |
| 4 | D-glucono-δ-lactone | 25.0 | NaOH 1.0M | 270 | + |
| 5 | glycerophosphate | 15.0 | Acetic acid | − | − |
| 6 | L-serine | 15.0 | 50% v/v | − | 0 |
| 7 | glycine | 10.0 | | − | 0 |
| 8 | HES | 10.0 | | − | 0 |
| 9 | Solutol® | 5.0 | | − | 0 |
| 10 | Kollidon® | 5.0 | | − | 0 |

0 = normal;
− = inferior stability;
+ = superior stability

Shelf Life Estimation (25° C.)

The shelf life period (10% potency loss) of the samples at 25° C. has been estimated by generating an Arrhenius model on basis of the data from the 48-days-hydrolysis study of Rocuronium bromide (see Table 2).

An approximated estimation of shelf life is made with the characteristic kinetics plots. Experimentally it is measured how the concentration of Rocuronium changes as the hydrolysis reaction progresses. This method is an approximation so experimental data suffers from random error and in a first screening of formulations are not studied at several temperatures.

The rate constant at each temperature is determined using a scatter plot of time versus Rocuronium concentration by a kinetic zero order reaction and versus the natural logarithm of the Rocuronium concentration by a kinetic first order reaction and their integrated rate law.

| Reaction Order | Integrated rate law | Kinetic plot | Slope | Arrhenius Equation | Arrhenius plot |
|---|---|---|---|---|---|
| Zero | $[ROC] = [ROC]_0 - Kt$ | $[ROC]$ vs. t | $-K$ | $\ln K = \ln A - (E/RT)$ | $\ln K$ vs. $1/T$ |
| First | $[ROC] = [ROC]_0\, e^{-Kt}$ | $\ln[ROC]$ vs. t | $-K$ | | |

[ROC] = Rocuronium concentration,
[ROC]0 = initial Rocuronium concentration,
K = rate constant,
t = time,
T = Temperature,
A = pre-exponential factor,
E = activation energy From the Arrhenius plot it is possible to determine the values of A and E. With these parameters it is possible to use the Arrhenius equation to project the rate constant at any temperature.

Once the rate constant at the desired temperature (such as 25° C.) is obtained the shelf life is estimated through the respective kinetic reaction order.

TABLE 2

Shelf life estimation

| | | Shelf life estimation (months) 90% confidence level, 25° C. | |
|---|---|---|---|
| No. | Formulation | Zero Order (K degradation) | 1st order (K degradation) |
| 1 | 0.33% NaCl | 18.7 | 19.9 |
| 2 | 2.0% D-glucose | 32.2 | 34.7 |
| 3 | 2.0% D-mannitol | 36.4 | 39.6 |
| 4 | 2.5% D-glucono-δ-lactone | 119.4 | 130.8 |
| 5 | 1.5% glycerophosphate | 15.0 | 16.4 |
| 6 | 1.5% L-serine | 63.2 | 70.2 |
| 7 | 1.0% glycine | 35.6 | 40.2 |
| 8 | 1.0% HES | 20.5 | 22.3 |
| 9 | 0.5% Solutol® | 36.9 | 41.1 |
| 10 | 0.5% Kollidon® | 8.9 | 9.6 |

Example 2

Hydrolysis of Rocuronium (9 weeks, 55° C.)

In 5 mL Mini-Plasco® vials Rocuronium bromide (10 mg/mL), the excipients (see Table 3) and sodium acetate.3H$_2$O (2.0 mg/mL) have been dissolved in water. The pH value of the solution has been adjusted by the addition of acetic acid (50% v/v) or sodium hydroxide (1.0 M). Then the formulations were autoclaved using cycles optimized for its formats and put into the stability chambers at a temperature of 55±3° C. The formulations were analyzed after 7, 18, 20, 32, 33, 46, 47 and 61 days. The assessment of the stability of the solutions has been made on basis of the appearance of the solutions, the pH-value, osmolality, content of Rocuronium and its respective hydrolyzed product (Des-17-acetyl Rocuronium) determined by HPLC (method adapted for Rocuronium Bromide, British Pharmacopoeia 2008).

TABLE 3

Formulations of Example 2

| Sample | Excipient | (mg/mL) | pH adjustment | (pH) |
|---|---|---|---|---|
| 1 | NaCl | 3.3 | Acetic acid | 3.3 |
| 2 | NaCl | 3.3 | 50% v/v | 4.0 |
| 3 | D-Glucose | 20 | | 4.0 |
| 4 | D-Mannitol | 20 | | 4.0 |
| 5 | Glycine | 10 | | 4.0 |
| 6 | D-glucono-δ-lactone | 25 | NaOH 1.0M | 3.3 |
| 7 | D-glucono-δ-lactone | 25 | | 4.0 |

The concentration of hydrolyzed Rocuronium (Des-17-acetyl-Rocuronium) in the individual samples as determined by HPLC are shown in FIG. 1. As apparent from FIG. 1, Rocuronium solutions containing D-glucono-δ-lactone are significantly more stable against hydrolysis than solutions containing other excipients.

Example 3

Mannitol a Commonly Used Excipient is Compared with D-Glucono-δ-Lactone at the Same Concentration Level:

In 10 mL Mini-Plasco® vials Rocuronium bromide (10 mg/mL), the excipients (see Table 4) and sodium acetate.3H$_2$O (2.0 mg/mL) have been dissolved in water. Then the formulations were autoclaved using cycles optimized for its formats and put into the stability chambers at a temperature of 25±2° C./60±5% R.H, 40±2° C./75±5% R.H and 55±3° C. The formulations were analyzed after 0, 7, 19 and 33 days. The assessment of the stability of the solutions has been made on basis of the appearance of the solutions, the pH-value, osmolality, content of Rocuronium and its respective hydrolyzed product (Des-17-acetyl Rocuronium) determined by HPLC (method adapted for Rocuronium Bromide, British Pharmacopoeia 2008).

TABLE 4

Formulations of Example 3

| | | Formulations | |
| --- | --- | --- | --- |
| | Raw Material | FA | FB |
| Active Ingredient | Rocuronium bromide (g) | 1.00 | 1.00 |
| Buffering Agent | Sodium Acetate•H$_2$O (mg) | 200.0 | 500.0 |
| | Sodium Citrate•H$_2$O (mg) | — | 500.0 |
| pH Adjuster | Acetic Acid 50% q.s.p. | pH 3.8-4.2 | Without adjustment |
| Tonicity Agent | Gluconolactone (g) | — | 2.5 |
| | Mannitol (g) | 2.5 | — |
| Solvent | Water for injections (ml) | 100.0 | 100.0 |
| | Osmolality (mOsm/Kg) | 321 | 298 |
| | pH solution | 3.8-4.2 | 3.8-4.2 |

Figure 2:
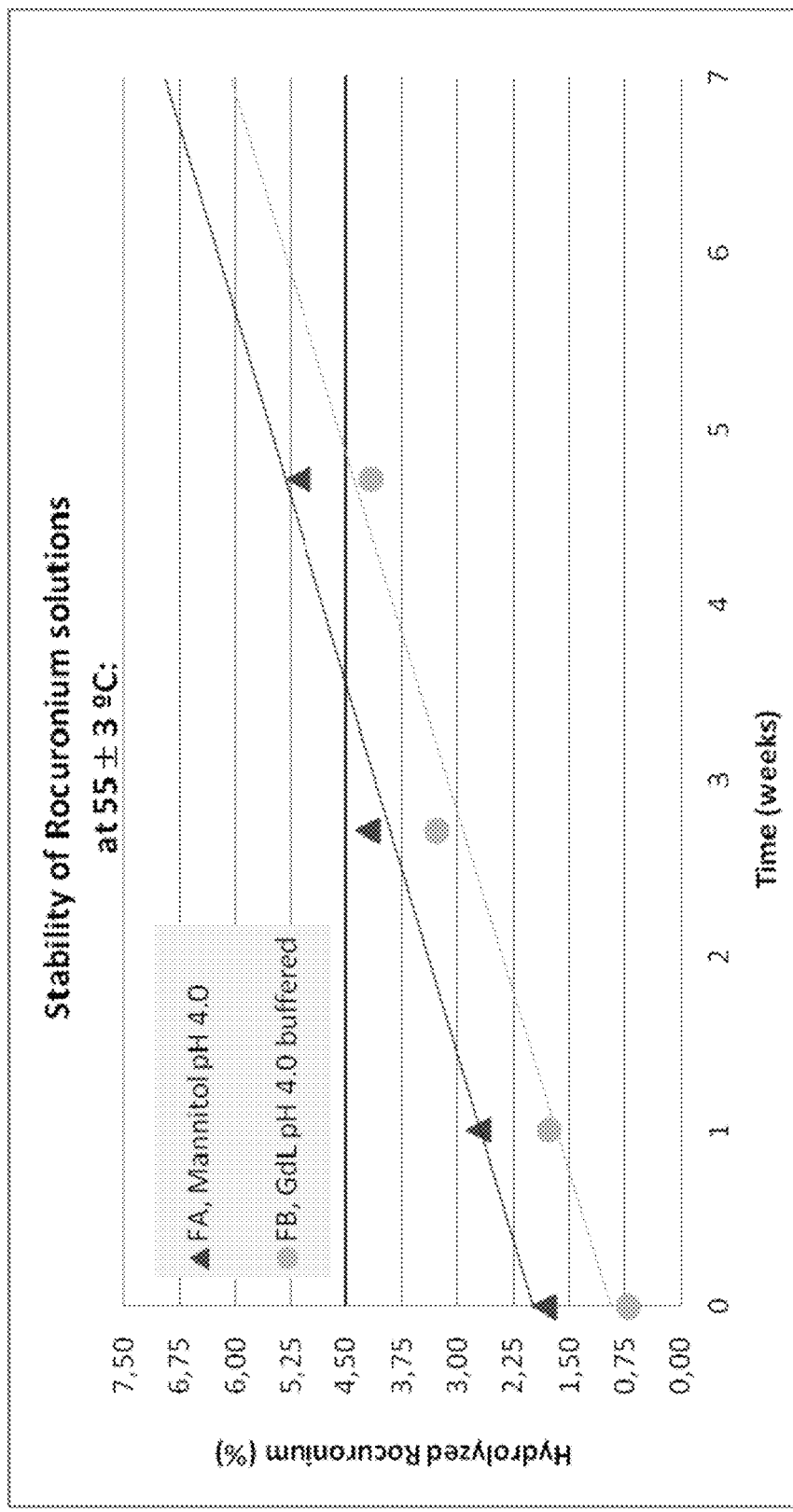
FIG. 2 is a diagram showing that Rocuronium solutions containing D-glucono-delta-lactone are more stable against hydrolysis than a solution containing mannitol.

The concentration of hydrolyzed Rocuronium (Des-17-acetyl-Rocuronium) in the individual samples as determined by HPLC are shown in FIG. 2. As apparent from FIG. 2, Rocuronium solutions containing D-glucono-δ-lactone are significantly more stable against hydrolysis than the solution containing mannitol.

The invention claimed is:

1. An aqueous solution comprising:
   (i) a steroidal neuromuscular blocking agent, wherein the steroidal neuromuscular blocking agent is rocuronium bromide, further wherein the steroidal neuromuscular blocking agent is present in the aqueous solution at a concentration ranging from 9 mg/mL to 11 mg/mL based on the total volume of the aqueous solution;
   (ii) an excipient that is D-gluconic acid and D-glucono-delta-lactone, wherein the excipient is present in the aqueous solution at a concentration ranging from 24 mg/mL to 26 mg/mL based on the total volume of the aqueous solution; and
   (iii) a buffering agent, wherein the buffering agent comprises sodium acetate, sodium citrate, or a combination thereof,
   wherein the solution has a pH ranging from 3.8 to 4.2.

2. The aqueous solution of claim 1, wherein a ratio of the D-gluconic acid to the D-glucono-delta-lactone ranges from about 20:1 to about 1:20.

3. The aqueous solution of claim 1, wherein the buffering agent further comprises a phosphate.

4. The aqueous solution of claim 1, wherein the osmolality of the aqueous solution ranges from 270 mOsm/kg to 340 mOsm/kg.

5. A liquid pharmaceutical composition comprising the aqueous solution of claim 1, wherein the rocuronium bromide concentration of the liquid pharmaceutical composition is 9 mg/mL to 11 mg/mL, the excipient concentration is 24 mg/mL to 26 mg/mL and the pH ranges from 3.8 to 4.2.

6. A muscle relaxant or anesthetic comprising the liquid pharmaceutical composition of claim 5, wherein the rocuronium bromide concentration of the liquid pharmaceutical composition is 9 mg/mL to 11 mg/mL, the excipient concentration is 24 mg/mL to 26 mg/mL and the pH ranges from 3.8 to 4.2.

7. The aqueous solution of claim 1, wherein the buffering agent is present in the aqueous solution at a concentration in the range of from 0.5 mg/mL to 50 mg/mL based on the total volume of the aqueous solution.

8. The aqueous solution of claim 1, wherein the steroidal neuromuscular blocking agent is present in the aqueous solution at a concentration of 10 mg/mL based on the total volume of the aqueous solution.

9. The aqueous solution of claim 1, wherein the excipient is present in the aqueous solution at a concentration of 25 mg/mL based on the total volume of the aqueous solution.

10. The aqueous solution of claim 1, wherein the steroidal neuromuscular blocking agent is present at a concentration of 10 mg/mL and the excipient is present at a concentration of 25 mg/mL based on the total volume of the aqueous solution.

11. A method for delivering the aqueous solution of claim 1 to a patient, comprising delivering the solution of claim 1 to the patient via an injection, wherein the composition relaxes one or more skeletal muscles of the patient.

* * * * *